(12) United States Patent
Murase

(10) Patent No.: US 9,795,292 B2
(45) Date of Patent: Oct. 24, 2017

(54) METHOD FOR TAKING TOMOGRAPHIC IMAGE OF EYE

(71) Applicant: NIDEK CO., LTD., Gamagori-shi, Aichi (JP)

(72) Inventor: Yuji Murase, Gamagori (JP)

(73) Assignee: NIDEK CO., LTD., Aichi (JP)

( * ) Notice: Subject to any disclaimer, the term of this patent is extended or adjusted under 35 U.S.C. 154(b) by 186 days.

(21) Appl. No.: 13/780,637

(22) Filed: Feb. 28, 2013

(65) Prior Publication Data

US 2013/0222566 A1 Aug. 29, 2013

(30) Foreign Application Priority Data

Feb. 29, 2012 (JP) .................................. 2012-044069
Feb. 29, 2012 (JP) .................................. 2012-044070

(51) Int. Cl.
*H04N 9/47* (2006.01)
*A61B 3/113* (2006.01)
*A61B 3/10* (2006.01)
*G01B 9/02* (2006.01)

(52) U.S. Cl.
CPC .............. *A61B 3/113* (2013.01); *A61B 3/102* (2013.01); *G01B 9/02076* (2013.01); *G01B 9/02091* (2013.01); *F04C 2270/041* (2013.01); *G01B 2290/65* (2013.01)

(58) Field of Classification Search
CPC ...................................................... A61B 3/113
USPC ......................................................... 348/78
See application file for complete search history.

(56) References Cited

U.S. PATENT DOCUMENTS

| 8,556,424 B2 | 10/2013 | Katayama |
| 8,983,164 B2 | 3/2015 | Iwase |
| 2010/0110171 A1* | 5/2010 | Satake ........................... 348/78 |
| 2010/0142780 A1 | 6/2010 | Yasuno et al. |
| 2011/0069279 A1 | 3/2011 | Hacker et al. |
| 2011/0222020 A1 | 9/2011 | Izatt et al. |
| 2011/0267340 A1* | 11/2011 | Kraus et al. ................... 345/419 |
| 2012/0033181 A1 | 2/2012 | Koizumi et al. |

FOREIGN PATENT DOCUMENTS

| EP | 1775545 A2 | 4/2007 |
| EP | 2420181 A1 | 2/2012 |
| JP | 2010-110392 A1 | 5/2010 |
| JP | 2011019644 A2 | 2/2011 |
| JP | 2011254959 A2 | 12/2011 |

OTHER PUBLICATIONS

Extended European Search Report dated Jun. 18, 2013 corresponds to European Patent Application No. 13157287.7.

(Continued)

*Primary Examiner* — Farzana Hossain
(74) *Attorney, Agent, or Firm* — Rankin, Hill & Clark LLP

(57) ABSTRACT

A method for capturing a tomographic image of an eye includes: obtaining a plurality of tomographic images of an examinee's eye by an optical scanning; obtaining a displacement distribution that is a distribution of a displacement for each A-scan among the plurality of tomographic images; and correcting a displacement among the tomographic images based on the displacement distribution.

12 Claims, 4 Drawing Sheets

(56) References Cited

OTHER PUBLICATIONS

Official Communication pursuant to Rule 114(2) EPC issued on Mar. 13, 2017 with the Third party observations filed on Mar. 7, 2017 for European Patent Application No. 13157287.7.
Juan Xu, et.al., "Alignment of 3-D Optical Coherence Tomography Scans to Correct Eye Movement Using a Particle Filtering," IEEE Transaction on Medical Imaging, vol. 31, No. 7, Jul. 2012 (Date of publication Jan. 4, 2012), pp. 1337-1435.; Cited in EP Official Communication.

* cited by examiner

METHOD FOR TAKING TOMOGRAPHIC IMAGE OF EYE

CROSS-REFERENCE TO RELATED APPLICATION

This application is based on Japanese Patent Application Nos. 2012-44069 and 2012-044070 filed with the Japan Patent Office on Feb. 29, 2012, the entire content of which are hereby incorporated by reference.

BACKGROUND

1. Technical Field

The present invention relates to a method for capturing a tomographic image of an eye.

2. Related Art

A tomographic imaging apparatus takes a tomographic image of an eye by using optical coherence tomography (OCT: Optical Coherence Tomography), for example. This apparatus uses an optical scanner to scan a fundus by a measurement light. Thereby, the tomographic image of the eye (for example, the tomographic image of the fundus) is obtained. The obtained tomographic image is utilized for evaluating the conditions of the eye (JP 2010-110392 A).

Such an apparatus obtains multiple tomographic images for averaging the noise components included in the tomographic image. This apparatus obtains an averaging image based on these multiple tomographic images. This apparatus obtains multiple tomographic images for substantially the same part, for example. Then, the luminance values of the tomographic images are summed for each pixel to derive the average value. This allows an averaging image to be obtained.

The position of the tomographic image deviates as the position of the eye deviates during image acquisition. Therefore, such displacement is corrected by the parallel movement and/or the rotation movement of the image. For example, the apparatus disclosed in JP 2010-110392 A divides the tomographic image with respect to the scan direction and corrects the displacement for each divided area.

SUMMARY

A method for capturing a tomographic image of an eye includes: obtaining a plurality of tomographic images of an examinee's eye by an optical scanning; obtaining a displacement distribution that is a distribution of a displacement for each A-scan among the plurality of tomographic images; and correcting a displacement among the tomographic images based on the displacement distribution.

DETAILED DESCRIPTION

Figure 1:
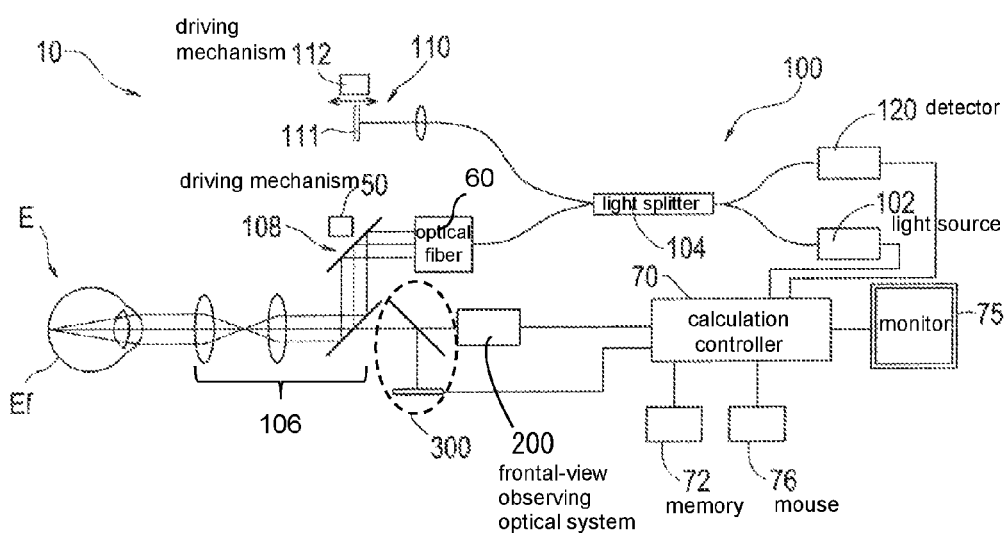
FIG. 1 illustrates a tomographic imaging apparatus according to the present embodiment.

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

The corrections of the displacement as described above do not necessarily result in a preferable tomographic image.

One of the purposes of the present disclosure is to provide a method for capturing a tomographic image that allows for obtaining the preferable tomographic image that is suitable for observation and/or analysis.

A method for capturing a tomographic image of an eye (hereafter, referred to as the method) includes: obtaining a plurality of tomographic images of an examinee's eye by an optical scanning; obtaining a displacement distribution that is a distribution of a displacement for each A-scan among the plurality of tomographic images; and correcting a displacement among the tomographic images based on the displacement distribution.

According to the present method, the preferable tomographic image suitable for observation and/or analysis can be obtained.

The inventor has found that a distortion of the position of the apparatus to the eye (alignment deviation) and/or a deviation in the fixation direction cause a distortion of the form in the tomographic image. Such distortion has been of a component that is difficult to be corrected by the general parallel movement and the rotation movement of the image. It is understood that the occurrence of such distortion is caused by, for example, the fact that the optical path length in the scan changes depending on the light incidence position to the eye (see, for example, FIGS. 8A to 8C).

Further, the inventor has found that the movement of the eye in the direction parallel to the scan direction of the light or the aberration of the optical system causes the change in the magnification with respect to the scan direction among the tomographic images of the same examinee's eye, and such a change results in the distortion of the tomographic image with respect to the scan direction.

One embodiment of the tomographic imaging apparatus according to the present disclosure will be described based on the drawings.

<Outline>

The tomographic imaging apparatus according to the present embodiment (hereafter, referred to as the apparatus) obtains a plurality of tomographic images of the eye that include an A-scan signal obtained by the optical scan in the lateral direction. The apparatus obtains a distribution of the displacements of the object tomographic image to the reference tomographic image for each A-scan (the displacement distribution). Based on the obtained displacement distribution, the apparatus corrects the displacement among the tomographic images on an A-scan basis.

The optical path length changes between at the center part and at the peripheral part of the photographed part (the scan area) due to the deviation of the incidence position of the light to the eye. The imaging scheme in the apparatus (hereafter, referred to as the scheme) is advantageous for correcting the displacement among the tomographic images that is caused by the above change. The scheme can be applied to the apparatus for capturing the tomographic image of the fundus, the anterior segment, and/or the entire eyeball.

The apparatus obtains a plurality of tomographic images of the eye that include the A-scan signal obtained by the optical scan in the lateral direction. The apparatus obtains a plurality of tomographic images at a predetermined scan width, for example. The apparatus corrects the deviation of the magnification with respect to the scan direction among the plurality of tomographic images.

The scheme is advantageous for correcting the deviation of the magnification with respect to the scan direction among the tomographic images. Such correction is advantageous for the case where the scan range of the eye changes in response to the movement of the eye during the scan, for example. Further, the scheme is advantageous for the case where there is a difference between at the center and at the peripheral of the view angle due to the distortion aberration of the OCT system. The scheme can be applied to the apparatus for capturing the tomographic image of the fundus, the anterior segment, and/or the entire eyeball.

It is noted that the correction of the displacement based on the displacement distribution for each A-scan and the correction of the deviation of the magnification with respect to the scan direction can be performed separately. Also, these corrections can be performed together.

<Fundamental Configuration>

The apparatus includes a photographing device having an optical coherence tomography (OCT), for example. This photographing device generates tomographic images. As illustrated in FIG. 1, this photographing device (OCT device) 10 includes a coherent optical system 100 having a measurement optical path and a reference optical path. The coherent optical system 100 has a light source 102, a light splitter (for example, a coupler, a circulator, and the like) 104, an optical scanner 108, a light combiner (for example, a coupler, a circulator, and the like) 104, and an optical detector (hereafter, referred to as the detector) 120. The light splitter splits the light generated from the light source into the measurement optical path and the reference optical path. The scanner 108 scans the part to be photographed in the lateral direction by the light guided from the light source. The light combiner 104 combines a measurement light from the measurement optical path and a reference light from the reference optical path. The detector 120 detects the interference state of the measurement light from the measurement optical path and the reference light from the reference optical path.

A calculation controller (an image processor) 70 obtains depth information (A-scan signal) by processing the output signal from the detector 120. When obtaining the tomographic image of the fundus, the calculation controller 70 controls the optical scanner 108 to scan the eye in the lateral direction by the measurement light. Thereby, the calculation controller 70 obtains the depth information at the scan position. The calculation controller 70 aligns, in the scan direction, the depth information for each scan position. Thereby, the tomographic image of the fundus is obtained.

When obtaining an averaging image, the calculation controller 70 scans a particular scan position in the lateral direction (the lateral position) for multiple times by the measurement light. Thereby, multiple tomographic images are obtained. The calculation controller 70 controls the optical scanner 108 to obtain in advance the multiple tomographic images with respect to the same position on the fundus. The obtained multiple tomographic images are stored in a memory 72. The number of the obtained tomographic images is at least two or more, may be ten or more, and may be a hundred or more. The calculation controller 70 corrects the displacement among the obtained tomographic images. After the correction of the displacements, the calculation controller 70 sums these tomographic images to obtain an averaged tomographic image (an averaging image). The calculation controller 70 displays the averaging image on a monitor 75.

When obtaining OCT three-dimensional data, the calculation controller 70 controls the optical scanner 108 to scan (for example, to raster-scan) the fundus two-dimensionally by the measurement light. In such the way, the calculation controller 70 obtains in advance multiple tomographic images according to the different lateral positions. The obtained multiple tomographic images are stored in the memory 72. The calculation controller 70 corrects the displacement between the neighboring tomographic images by using the obtained multiple tomographic images. This correction allows the calculation controller 70 to reconstruct the OCT three-dimensional data. The calculation controller 70 analyzes the OCT three-dimensional data. This allows the calculation controller 70 to obtain an analysis result such as a layer thickness map, a three-dimensional graphic, and the like. The calculation controller 70 displays the obtained analysis result on the monitor.

<Correction of Deviation of the Forming Position of A-Scan Signal Among Tomographic Images (See FIG. 4 and FIG. 5)>

The calculation controller 70 detects the information of the displacement between the reference tomographic image and the object tomographic image in at least two, that is, a plurality of areas. Based on the detection result, the calculation controller 70 obtains a distribution of the displacements of the object tomographic image to the reference tomographic image for each A-scan (the A-scan displacement distribution).

For example, the calculation controller 70 derives the information of the displacement between the reference tomographic image and the object tomographic image in the plurality of areas of the tomographic image (the displacement information). The calculation controller 70 derives an approximation function based on the displacement information for each area. Thereby, the calculation controller 70 derives the A-scan displacement distribution as described above.

In another scheme, the calculation controller 70 extracts a feature point of the reference tomographic image for each A-scan. Further, the calculation controller 70 extracts a feature point of the object tomographic image for each A-scan. The calculation controller 70 derives the distribution of the feature point in the reference tomographic image for each A-scan (the feature point distribution) and the feature point distribution in the object tomographic image, respectively. The calculation controller 70 derives the deviation of the feature point distribution between the reference tomographic image and the object tomographic image. Thereby, the calculation controller 70 obtains the A-scan displacement distribution described above.

The calculation controller 70 corrects the forming position of the A-scan signal in the object tomographic image based on the A-scan displacement distribution. This allows the calculation controller 70 to reconstruct the object tomographic image. Thus, the morphologic distortion of the object tomographic image to the reference tomographic image is corrected.

According to the above-described scheme, the deviation (distortion) among the tomographic images caused by the alignment deviation or the deviation in the fixation direction is corrected on an A-scan signal basis (or an A-scan basis).

It is noted that the A-scan displacement distribution is obtained in at least either one of the scan direction and the depth direction. The calculation controller 70 corrects the displacements among the tomographic images by using the A-scan displacement distribution with respect to at least either one of the scan direction and the depth direction.

Figure 8A:
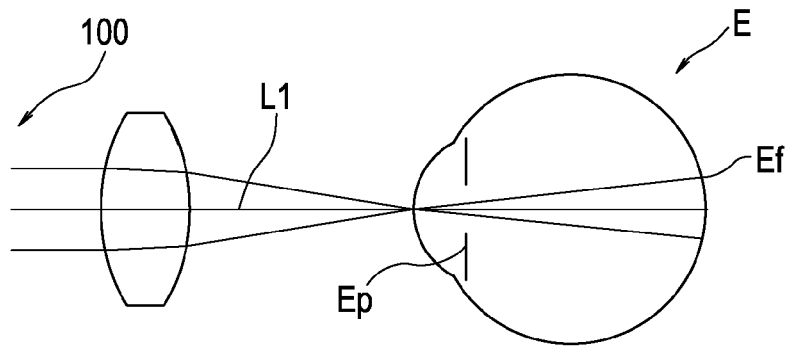
FIGS. 8A to 8C are views for illustrating changes in optical path length due to a deviation of the light incidence position with respect to the eye.
Figure 8B:
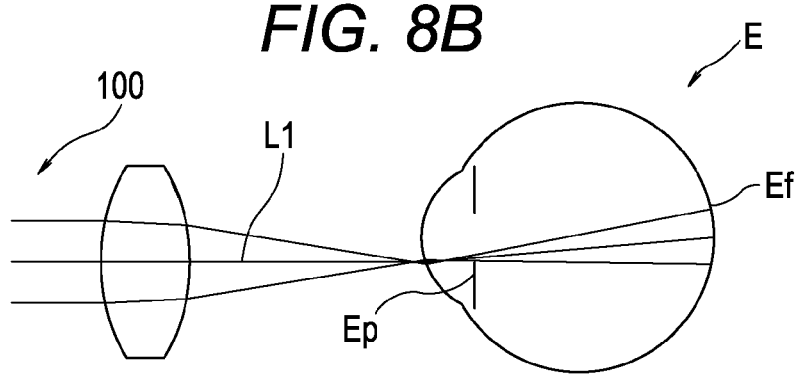
Figure 8C:
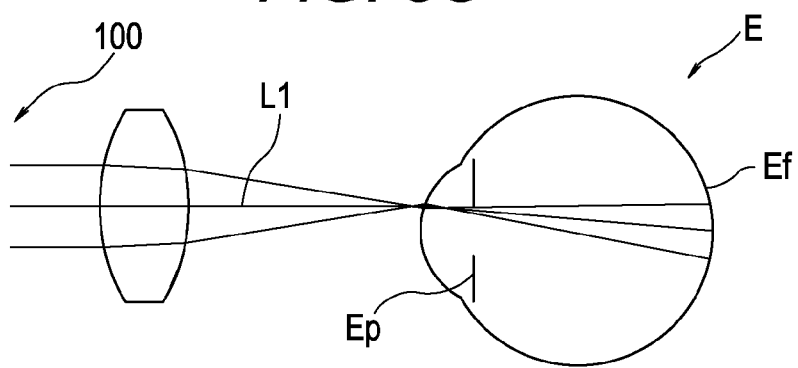

It is noted that the above-described correction process is advantageous in particular for the case where the tomographic image is displayed relatively horizontally on the monitor 75. For example, when the area of 2 mm in vertical length by 9 mm in horizontal length in the actual dimension is formed as a tomographic image of the aspect ratio of 1:2, the deviation in the Z direction (the optical path length direction) will be highlighted. As illustrated in FIGS. 8A to 8C, when the incidence position of the measurement light to the eye deviates with respect to the direction orthogonal to the light axis L1, the difference in the optical path length of the measurement light between at the center point and at the peripheral point of the eye will be larger. This difference in the optical path length affects the forming position of the tomographic image with respect to the Z direction. Therefore, the difference in the optical path length appears as the distortion in the tomographic image. It is noted that, as discussed above, the optical path length of the measurement light changes from the center to the peripheral. Thus, there is a high likelihood that, according to the position correction on an image basis such as the rotation of the image, the forming positions of the A-scan signal in the tomographic images obtained according to the scan position (the scan direction) do not match.

As seen in the above-described scheme, obtaining the averaging image by using the corrected tomographic image allows for the preferable correction of the deviation among the tomographic images. Therefore, a clear tomographic image with little noise can be obtained. Further, a use of the tomographic image corrected by the above-described scheme allows the preferable OCT three-dimensional data to be obtained. It is noted that the neighboring tomographic images are made of substantially the same organization. Therefore, the neighboring tomographic images can be utilized for the correction.

<Magnification Correction with Respect to Scan Direction (see FIG. 6 and FIG. 7)>

The calculation controller 70 corrects the deviation of the magnification so that the magnifications with respect to the scan direction match by the image processing of a plurality of tomographic images. For example, the calculation controller 70 corrects the deviation of the magnification with respect to the scan direction among the tomographic images by comparing the reference tomographic image and the object tomographic image. Specifically, the calculation controller 70 obtains the information of the deviation of the scan width on the eye among the tomographic images. Based on the obtained deviation information of the scan width, the calculation controller 70 corrects the deviation of the magnification with respect to the scan direction among the tomographic images. The calculation controller 70 obtains the deviation information of the scan width based on the distance among at least two feature areas in each tomographic image.

Further, without limited to the above, the calculation controller 70 may expand or reduce the object tomographic image to the reference tomographic image so as to have the same magnification for the reference tomographic image and the object tomographic image. Thereby, the calculation controller 70 may correct the deviation of the magnification with respect to the scan direction among the tomographic images.

There is a scheme in which a plurality of tomographic images is not used. In this scheme, the apparatus includes an eye movement detection sensor (for example, a frontal-view observing optical system 200) for detecting the movement of the eye during the optical scanning. The calculation controller 70 obtains the information of the deviation of the scan width on the eye during the optical scanning based on the detection result by the detection sensor. The calculation controller 70 corrects the magnification with respect to the scan direction of the tomographic image based on the obtained deviation information of the scan width. The eye movement detection sensor can detect the movement of the eye during the optical scanning. The eye movement detection sensor may be such a device that can obtain 1000 images per one second (for example, a high-speed camera).

The calculation controller 70 detects, by the image processing, the displacement among the front images obtained in real time by the frontal-view observing optical system 200. This causes the calculation controller 70 to detect the displacement amount and the displacement direction with respect to the scan direction. When the displacement direction is the same as the scan direction, the calculation controller 70 may decrease the magnification of the tomographic image with respect to the scan direction. Contrarily, when the displacement direction is opposite to the scan direction, the calculation controller 70 may increase the magnification of the tomographic image with respect to the scan direction.

The distortion of the magnification in the scan direction between the tomographic images can be preferably corrected by the above-described scheme. Therefore, a clear tomographic image (an averaging image) with little noise can be obtained. Further, the deviation of the magnification in the scan direction among the tomographic images can be preferably corrected by the above-described scheme. Therefore, the preferable OCT three-dimensional data can be obtained. It is noted that the neighboring tomographic images are made of substantially the same organization and thus can be utilized for the correction.

<Correction Process on an Image Basis>

It is noted that it is advantageous to utilize the above-described process (for example, at least one of the correction of the forming position of the A-scan signal and the magnification correction with respect to the scan direction) together with the correction process on an image (or a pixel) basis that forms the tomographic image. For example, after reconstructing the object tomographic image by the above-described process, the calculation controller 70 obtains the displacement information between the reference tomographic image and the object tomographic image on an image basis. The calculation controller 70 corrects the displacement between the tomographic images on an image basis by moving (parallel shifting, rotating, and the like) the image signal (or the pixel signal) that forms the object tomographic image. It is noted that, when the displacement is corrected on an image basis, the entire displacement of the tomographic image may be corrected all at once. Also, the tomographic image may be divided into a plurality of image areas to correct the displacement for each division area. It is noted that the correction may be performed using the above-described scheme after the correction process is performed on an image basis.

It is noted that it is advantageous to combine the displacement correction by the image processing as described above with the displacement correction in which the optical scanner 108 is controlled to correct the scan position in response to the displacement of the eye.

<Method, Program>

The technique of the present disclosure is not limited to the apparatus or the scheme described in the embodiment. For example, image processing software (program) for the tomographic image that performs the function of the above-described embodiment may be supplied to the system or the apparatus through the network or various storage mediums. Also, it is possible that the computer (for example, the CPU and the like) of the system or the apparatus reads out and executes the program. Of course, the above-described scheme of the embodiment can be applied to the processing method for the tomographic image.

<Application Other than for the Eye>

The present embodiment is also applicable to other apparatus than the apparatus for capturing the tomographic image of the eye. For example, the technique of the present embodiment can be also applied to the apparatus for capturing the tomographic image of biological tissues such as the skin of the human body, the blood vessel organization, and the like. Further, the technique of the present embodiment can be applied to the apparatus for capturing the tomographic image of the examined object other than the organism.

[Example]

The example in the apparatus of the present embodiment will be described below along the drawings. FIG. 1 is a view of the outline configuration illustrating the arrangement of the tomographic imaging apparatus according to the present embodiment. In the following description, an ophthalmologic photographing apparatus will be described as an example of the tomographic imaging apparatus. It is noted that the axis direction of an examinee's eye (eye E) is defined as the Z direction, the horizontal direction is defined as the X direction, and the perpendicular direction is defined as the Y direction in the present embodiment. The surface direction of the fundus is the XY direction.

The outline of the configuration of the apparatus will be described. The ophthalmologic photographing apparatus according to this example is an optical coherence tomography device (OCT device) 10 for capturing the tomographic image of the fundus Ef of the eye E. The OCT device 10 includes a coherent optical system (OCT system) 100, a frontal-view observing optical system 200, a fixation target projecting unit 300, and a calculation controller (CPU) 70.

The OCT system 100 includes a light source 102, a light receiving device (the detector 120), and an irradiation position changing unit. The light source 102 irradiates the measurement light to the fundus. The light receiving device (the detector 120) detects the interference state of the measurement light reflected by the fundus and the reference light. The irradiation position changing unit (for example, the optical scanner 108, the fixation target projecting unit 300) changes the irradiation position of the measurement light on the fundus Ef in order to change the photographing position on the fundus Ef. The calculation controller 70 controls the irradiation position changing unit based on the preset photographing position information. The calculation controller 70 obtains the tomographic image based on the light receiving signal from the detector 120.

<OCT System>

The OCT system 100 has the apparatus configuration of so called ophthalmic optical coherence tomography. In the OCT system 100, the coupler (the splitter) 104 splits the light irradiated from the light source 102 into the measurement light and the reference light. A measuring optical system 106 guides the measurement light to the fundus Ef of the eye E and guides the reference light to a reference light optical system 110. The detector (the light receiving device) 120 receives the interference light obtained by the coupling of the measurement light reflected by the fundus Ef and the reference light.

The detector 120 detects the interference state of the measurement light and the reference light. In the Fourier domain OCT, the spectral intensity of the interference light is detected by the detector 120. The depth profile in a predetermined range is obtained by the Fourier transform on the data of the spectral intensity. The Fourier domain OCT includes, for example, the Spectral-domain OCT (SD-OCT) and the Swept-source OCT (SS-OCT).

In the SD-OCT, the light source 102 is a low coherent light source (a wide range light source), for example. The detector 120 includes, for example, a spectral optical system (a spectral meter) that splits the interference light into each frequency component (each wavelength component). The spectral meter includes a diffraction grating and a line sensor, for example.

In the SS-OCT, the light source 102 is a wavelength scanning light source (the wavelength variable light source) that changes the irradiating wavelength at a high speed. The detector 120 includes a single light-receiving device, for example. The light source 102 includes a light source, a fiber ring resonator, and a wavelength selective filter, for example. The wavelength selective filter includes a combination of a diffraction grating and a polygon mirror or a Fabry-Perot etalon, for example.

The light irradiated from the light source 102 is split into the measurement light and the reference light by the coupler 104. The measurement light is irradiated into the air after passing through the optical fiber. The light flux is condensed at the fundus Ef via the optical scanner 108 and other optical members in the measurement light optical system 106. The light reflected by the fundus Ef returns to the optical fiber via the similar optical path.

The optical scanner 108 scans the fundus in the XY direction (the lateral direction) by the measurement light. The optical scanner 108 is disposed at the position conjugated with the pupil. The optical scanner 108 has two galvanometer mirrors, for example. The reflection angle of the galvanometer mirror can be adjusted to any angle by a driving mechanism 50.

The reflection (traveling) direction of the light flux irradiated from the light source 102 is changed by the galvanometer mirror. As a result, the fundus is scanned in any direction by the light flux. This causes the photographing position in the fundus Ef to be changed. The optical scanner 108 may be a reflection mirror (for example, a galvanometer mirror, a polygon mirror, a resonant scanner), an audio-optic modulator (AOM) for changing the traveling (polarizing) direction of the light, and the like.

The reference light optical system 110 generates the reference light. The reference light is coupled with the reflection light obtained in response that the measurement light is reflected by the fundus Ef. The reference light optical system 110 may be the Michelson system or the Mach-Zehnder system. The reference light optical system 110 includes, for example, a catoptric system (for example, a reference mirror). The catoptric system reflects the light from the coupler 104 to return it to the coupler 104. This causes the light to be guided to the detector 120. In another example, the reference light optical system 110 includes a transmission optical system (for example, an optical fiber). The transmission optical system transmits the light from the coupler 104 without returning it. Then, the light is guided to the detector 120.

In the OCT device 10, at least a part of the optical members disposed in the OCT system (the interference optical system) 100 is moved in the light axis direction. This allows for the adjustment of the difference in the optical path length between the measurement light and the reference light. For example, the reference light optical system 110 moves the optical member (for example, a reference mirror 111) in the reference light path. This allows for the adjustment of the difference in the optical path length between the measurement light and the reference light. For example, the reference mirror 111 is moved in the light axis direction by a driving mechanism 112. The arrangement for changing the difference in the light path length may be disposed in the measurement light path of the measuring optical system 106. In this case, the optical member (for example, the end of the optical fiber 60) disposed in the measurement light path is moved in the light axis direction. It is noted that a unit housing incorporating the entire OCT system 100 may be moved with respect to the eye E. This also allows for the adjustment of the difference in the light path length.

<Frontal-View Observing Optical System>

The frontal-view observing optical system (the observing optical system) 200 is provided for obtaining the frontal-view of the fundus Ef. The frontal-view observing optical system 200 may have the apparatus configuration of so called ophthalmic scanning laser ophthalmoscope (SLO), for example. The frontal-view observing optical system 200 includes an optical scanner and a second light receiving device, for example. The optical scanner scans the fundus two-dimensionally by the measurement light (for example, the infrared light) generated from the light source 102. The second light receiving device receives the fundus reflection light through a confocal opening disposed in a position substantially conjugated with the fundus.

It is noted that the frontal-view observing optical system 200 may have the arrangement of so called fundus camera type. Further, the OCT system 100 may serve also as the frontal-view observing optical system 200. That is, the front image may be an integrated image in the depth direction of the three-dimensional tomographic image, an integrated value of the spectral data at each position in the XY direction, and the like.

<Fixation Target Projecting Unit>

The fixation target projecting unit 300 has an optical system for guiding the direction of the visual line of the eye E. The fixation target projecting unit 300 has a fixation target presented to the eye E and can guide the eye E in a plurality of directions.

For example, the fixation target projecting unit 300 has a visible light source generating the visible light. The fixation target projecting unit 300 changes the presented position of the fixation target two-dimensionally. This causes the direction of the visual line to be changed and, as a result, the part to be photographed is changed. For example, when the fixation target is presented to the examinee's eye from the direction extended from photographing optical axis, the center part of the fundus is set as a part to be photographed. Further, when the fixation target is presented to the examinee's eye from above the photographing optical axis, the upper part of the fundus is set as a part to be photographed. That is, the part to be photographed is changed according to the position of the fixation target with respect to the photographing optical axis.

The fixation target projecting unit 300 may have any configuration. The fixation target projecting unit 300 may include LEDs aligned in a matrix, for example. In this configuration, the fixation position is adjusted by the lighting position of the LEDs. Alternatively, the fixation target projecting unit 300 may include an optical scanner for controlling the light from the light source, for example. In this configuration, the fixation position is adjusted by the lighting control of the light source. Further, the fixation target projecting unit 300 may be an internal fixation light type or an external fixation light type.

<Control Unit>

The calculation controller 70 controls the entire apparatus including the above-described members 100 to 300 and the members included therein. Further, the calculation controller 70 also serves as an image processing unit for processing the obtained image, an image analyzing unit for analyzing the obtained image, and the like. The calculation controller 70 is implemented with a general CPU (Central Processing Unit) and the like, for example.

Figure 2:
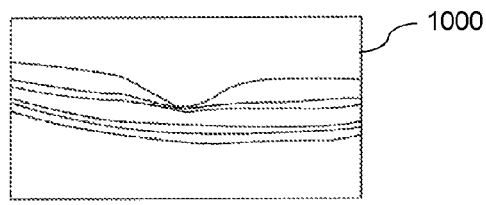
FIG. 2 illustrates an example of a tomographic image obtained by an OCT system.

FIG. 2 is an example of the tomographic image obtained by the OCT system 100. For example, the calculation controller 70 obtains the tomographic image 1000 (the OCT image) by the image processing based on the received signal output from the detector 120 of the OCT system 100.

A memory (storage unit) 72, a monitor 75, and a mouse (an operation input unit) 76 are electrically connected to the calculation controller 70, respectively. The calculation controller 70 controls the display screen of the monitor 75. The obtained fundus image is output on the monitor 75 as a static image or a motion image. Further, the fundus image is stored in the memory 72. The memory 72 stores various sorts of information regarding the photographing, for example. These sorts of information include the photographed tomographic image, the front image, and the information of the photographed position for each tomographic image. The calculation controller 70 controls respective members of the OCT system 100 based on the operation signal output from the mouse 76. It is noted that the detailed configuration of the above-described OCT device 10 is disclosed in Japanese Laid-open Patent Application Publication No. 2008-29467, for example.

In this example, one tomographic image (a B-scan image) is obtained in which the noise component is suppressed, for example. Therefore, a predetermined scan area is scanned for multiple times by the measurement light. Thereby, multiple tomographic images are obtained. The calculation controller 70 sums and averages the obtained multiple tomographic images. In this case, the calculation controller 70 divides each tomographic image into a plurality of areas with respect to the scanning direction of the measurement light. The division condition in each tomographic image is substantially the same. The calculation controller 70 detects the displacement among respective tomographic images for each divided area. This allows the calculation controller 70 to obtain the displacement information. Then, the calculation controller 70 corrects the displacement among the photographed images for each divided area based on the obtained displacement information. The calculation controller 70 then sums and averages the corrected photographed images.

More specifically, the calculation controller 70 first uses a scanning unit 23 to scan the predetermined scan area for multiple times by the measurement light. Thereby, a plurality (n (n≥2)) of tomographic images for substantially the same scan area are obtained and stored in the memory 72.

Figure 3:
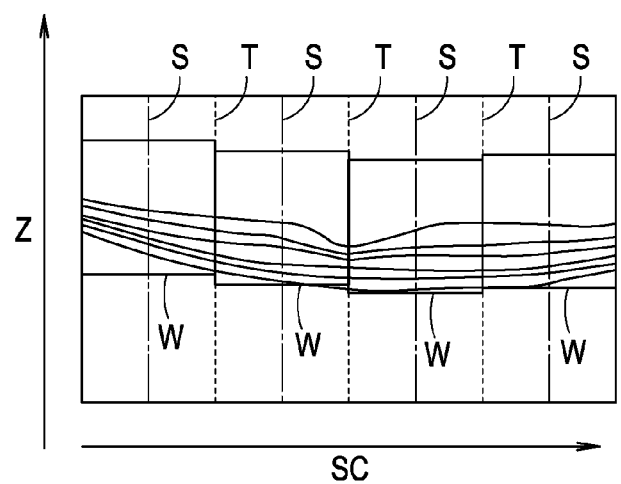
FIG. 3 is a view for illustrating the detection of a displacement and the division among the tomographic images.

A scheme for correcting the deviation (the displacement) among the tomographic images will be described below. The calculation controller 70 partitions each tomographic image by a predetermined width. Accordingly, the calculation controller 70 divides a tomographic image into a plurality of areas (see the dotted line T in FIG. 3). The calculation controller 70 divides each tomographic image into a plurality of areas with respect to the scanning direction (see the arrow SC in FIG. 3) of the measurement light.

Next, the calculation controller 70 searches a predetermined point that satisfies a predefined condition (for example, the point corresponding to the fundus surface, the point with the highest luminance) from the A-scan signal in each divided area (see the dashed line S in the figure). The calculation controller 70 sets the identified predetermined point (reference point) as a template position. The calculation controller 70 sets the image of some particular area (for example, the rectangular area) with respect to the template position as a template image (see the rectangular frame W in the figure). In such a way, the template image used for the displacement detection is set in the divided area.

The calculation controller 70 selects, as a reference image (a reference image), any one of n obtained tomographic images (for example, (n/2)th obtained image). The calculation controller 70 selects, as an object image, the tomographic image other than the reference image out of n obtained tomographic images. The calculation controller 70 sets the template image for the object image. In this case, the calculation controller 70 determines a template position in advance by the similar process to the reference image. This allows for the narrower searching range in the matching and thus allows for the faster processing.

The calculation controller 70 makes a comparison between the template image of the reference image and the template image of the object image for each divided area. Based on this comparison, the calculation controller 70 detects the displacement direction and the displacement amount of the object image to the reference image for each divided area. The calculation controller 70 shifts, on a pixel basis, the template image in the object image to the template image of the reference image, for example. Meanwhile, the calculation controller 70 calculates correlation values sequentially (on a pixel basis). The calculation controller 70 calculates, as the displacement amount, the deviation amount of the pixel when the correlation value is the maximum.

<Displacement Correction for Each A-Scan>

Figure 4:
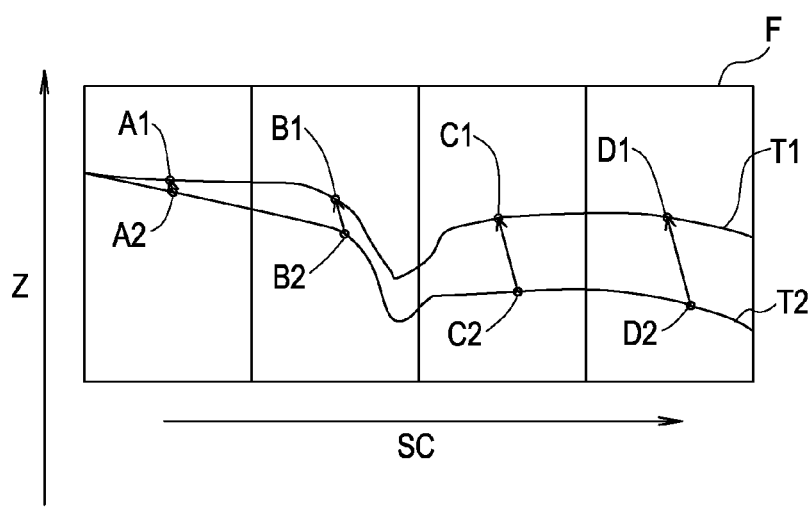
FIG. 4 is a view for illustrating deviations between a reference image and an object image.

FIG. 4 is a view for illustrating the deviation between the reference image and the object image. In the same manner as described above, detected are the displacement direction and the displacement amount of the A-scan signals corresponding to the reference points (A1 to D1, A2 to D2) located at the center of respective template images. A1 to D1 are the reference points in the reference image. A2 to D2 are the reference points in the object image. The calculation controller 70 derives the displacement information of the object image T2 to the reference image T1 for each A-scan signal for each reference point. Therefore, respective displacements for the scanning direction SC and the depth direction Z are derived.

The calculation controller 70 derives, for each point other than the reference point, the displacement information of the object image T2 to the reference image T1 for each A-scan. The relationship, at each point, between the reference image T1 and the object image (the compared image) T2 is identified with respect to the reference point in each tomographic image.

Figure 5:
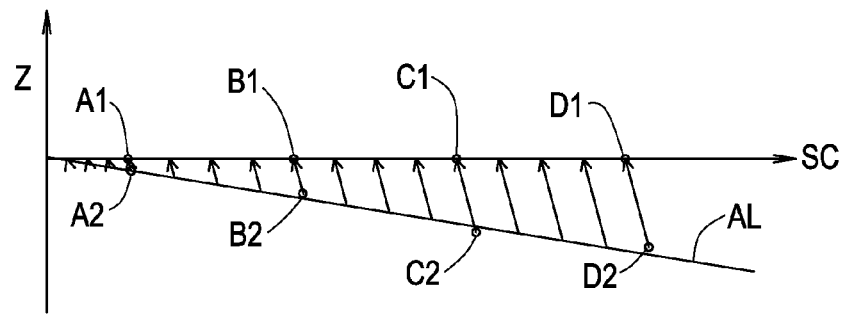
FIG. 5 illustrates a deviation for each A-scan of the object image to the reference image.

FIG. 5 is a graph illustrating the deviation between the reference image T1 and the object image T2 for each A-scan. The coordinates of the reference points A2 to D2 represent the displacement direction and the displacement amount at each reference point, and represent the displacement to the reference points A1 to D1 of the image. The calculation controller 70 implements the approximation process by the least-squares method in which the displacement amount is used at each reference point. According to this approximation process, the calculation controller 70 derives an approximate straight line (a regression line) AL with respect to the plurality of reference points A2 to D2. The approximate straight line AL is used as the information approximately representing the deviation between the reference image T1 and the object image T2 for each A-scan. The deviation information for each A-scan includes the deviation information of the depth direction Z and the deviation information of the scanning direction SC. It is noted that the regression line is not limited to the linear function such as the approximation straight line and may be an approximation curve based on the reference points.

As described above, the calculation controller 70 derives the displacement information between the reference image T1 and the object image T2 for each A-scan. Based on the derived displacement information, the calculation controller 70 moves, by the image processing, each A-scan signal (the luminance information in the depth direction) that forms the object image. As a result, the displacement is cancelled. The calculation controller 70 reconstructs the object image by the above process.

The calculation controller 70 utilizes the displacement information at each A-scan with respect to each A-scan signal to change the forming position of each A-scan. The calculation controller 70 corrects the displacement with respect to the A-scan signal corresponding to a particular point Ax. In this case, the calculation controller 70 may change the forming position of the A-scan signal at Ax in the object image so that the displacement amount (Scx, Zx) of the A-scan signal for Ax is offset. It is noted that, when changing the forming position of the A-scan signal, the calculation controller 70 may ignore, as unnecessary data, the part exceeding a frame (frame F) predefined for forming the tomographic image (for example, the upper end and lower end parts of the A-scan signal), or may save it as the image data.

It is noted that, for other tomographic images, the calculation controller 70 corrects the deviation to the reference image for each A-scan similarly to the above. Thereby, the calculation controller 70 reconstructs the tomographic image.

The above correction process allows for the correction of the displacement of each A-scan signal due to the deviation of the incidence position of the measurement light to the eye in response to the alignment deviation and/or the deviation of the fixation direction.

As described above, the displacement of the tomographic image is corrected for each A-scan. The corrected tomographic image is utilized for the creation of the averaging image. This allows the more accurate tomographic image (the averaging image) to be obtained. For example, the calculation controller 70 obtains the averaging image by summing the corrected tomographic images and deriving the averaging thereof.

The calculation controller 70 can utilize the absolute values of the real number component and the imaginary number component of the depth information forming each tomographic image to obtain the averaging image based on the plurality of tomographic images. Further, the calculation controller 70 can utilize the imaginary number component in the Z space that is the basis of each tomographic image to obtain the averaging image. The calculation controller 70 uses the real number component signal to obtain a first averaging data. Further, the calculation controller 70 uses the imaginary number component signal to obtain a second averaging data. Then, the calculation controller 70 is also able to combine the first average data and the second average data to obtain the averaging image based on the plurality of tomographic images.

The calculation controller 70 may correct the deviation on an image basis by moving the image for each divided area in addition to the displacement correction for each A-scan. This allows for more appropriate correction of the displacements among the tomographic images.

Further, the calculation controller 70 is also able to use the displacement-corrected tomographic image to perform an analysis (for example, a layer thickness analysis). This allows a preferable analysis result to be obtained.

It is noted that any tomographic image may be set as the tomographic image used for the reference image. For example, it is advantageous that the reference image is the tomographic image obtained under a state with little alignment deviation and fixation deviation. In this case, it is preferable that the OCT device 10 includes an anterior segment observing system. The OCT device 10 (the calculation controller 70) uses the anterior segment observing system to detect the alignment deviation. The use of the tomographic image with little alignment deviation as the reference image allows the preferable tomographic image to be obtained.

The scheme for detecting the information of the displacement between the reference image and the object image for each A-scan is not limited to the above-described scheme. For example, the calculation controller 70 extracts, for each A-scan signal, a feature point satisfying a predetermined condition in the A-scan signal that forms the tomographic image. The calculation controller 70 then obtains an approximation curve based on the extracted feature points. The calculation controller 70 derives the above-described approximation curves for the reference image and the object image, respectively. The calculation controller 70 derives the displacement between the approximation curve for the reference image and the approximation curve for the object image. The calculation controller 70 corrects the forming position of each A-scan signal so that the displacement is corrected. In this case, the calculation controller 70 uses the reference points, which are derived as described above, of the reference image and the object image to derive the relationship of the A-scan signals between the reference image and the object image.

For example, the calculation controller 70 extracts respective predetermined retinal layers (for example, the RPE layer (Retinal Pigment Epithelium)) for the reference image and the object image for each A-scan. Then, the calculation controller 70 obtains a distribution curve for the extracted retinal layers. The calculation controller 70 derives the distribution curves of the retinal layers for the reference image and the object image, respectively. The calculation controller 70 derives a displacement between the distribution curve for the reference image and the distribution curve for the object image. The calculation controller 70 corrects the forming position of each A-scan signal so that the displacement is corrected. In this case, the calculation controller 70 uses the images of the divided areas made of a plurality of A-scan signals to derive the relationship of the A-scan signals between the reference image and the object image.

<Magnification Correction with Respect to Scanning Direction>

Figure 6:
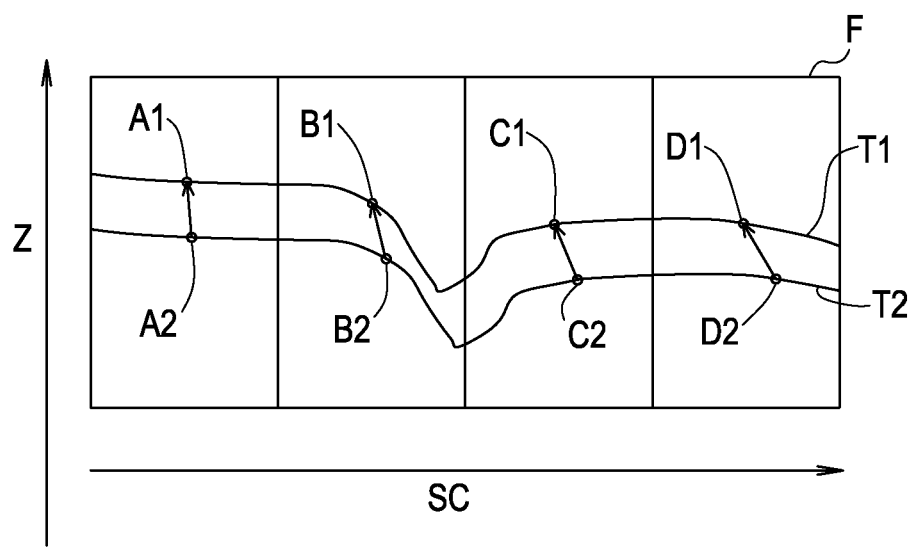
FIG. 6 is a view for illustrating deviations of the photographing range between the reference image and the object image.

FIG. 6 is a view for illustrating the deviation of the photographing range between the reference image and the objet image. When a plurality of tomographic images are obtained, the actual photographing range with respect to the scanning direction changes in response that the eye moves in parallel to the scanning direction of the measurement light. When the eye moves in parallel to the scanning direction of the measurement light, the actual photographing range will be narrower. Contrarily, (see FIG. 6), when the eye moves in the opposite direction of the scanning direction of the measurement light, the actual photographing range will be wider.

The calculation controller 70 extracts a plurality of feature areas in the tomographic image and derives the distance between the feature areas. Therefore, the calculation controller 70 obtains the deviation information of the scanning width. The positions of respective feature areas in the tomographic image are different with respect to the scanning direction SC in the tomographic image. The calculation controller 70 corrects the deviation of the magnification with respect to the scanning direction among the tomographic images based on the obtained deviation information of the scanning width.

The calculation controller 70 may correct the magnification after dividing the tomographic image into a plurality of areas. The calculation controller 70 divides the tomographic image with respect to the scanning direction. The calculation controller 70 extracts the feature area of each divided area. The calculation controller 70 calculates the distance between the neighboring feature areas (each interval between the reference points) for the reference image and the object image, respectively. The calculation controller 70 detects the distance between the neighboring feature areas of the reference image and the neighboring feature areas of the object image. The calculation controller 70 may correct the deviation of the magnification with respect to the scanning direction based on the detection result.

In such a way as described above, detected are the displacement direction and the displacement amount of the A-scan signal corresponding to the reference points (A1 to D1, A2 to D2) located at the center of each template image. A1 to D1 are the reference points in the reference image. A2 to D2 are the reference points in the object image. The calculation controller 70 derives, for each reference point, the displacement information of the object image T2 to the reference image T1 for each A-scan. Therefore, the displacements with respect to the scanning direction SC and the depth direction Z are derived, respectively.

Figure 7:
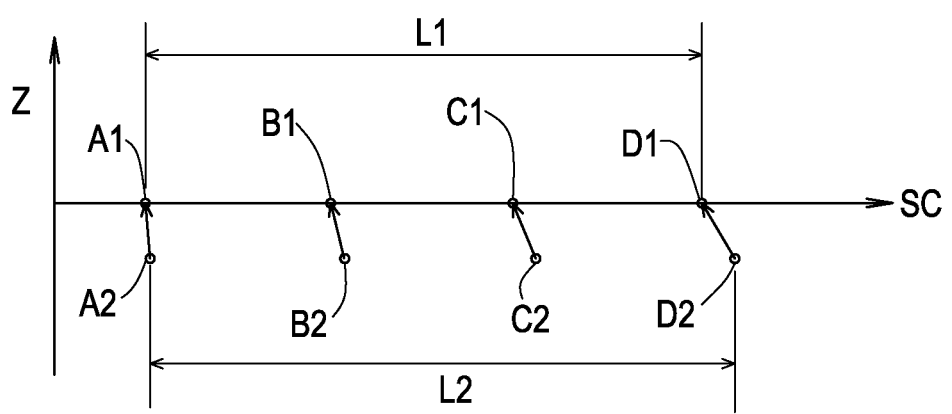
FIG. 7 illustrates deviations of the photographing range of the object image to the reference image.

FIG. 7 is a graph illustrating the deviation of the photographing range between the reference image T1 and the object image T2. For example, the calculation controller 70 calculates an interval L1 between two reference points in the reference image and an interval L2 between two reference points in the object image. The calculation controller 70 compares the interval L1 with the interval L2. This allows the calculation controller 70 to compare the actual scan widths (the scanning range on the eye with respect to the scanning direction) when a plurality of tomographic images are obtained at a predetermined scan width.

The calculation controller 70 corrects the magnification with respect to the scanning direction (for example, the lateral direction) in the object image so that the interval L2 in the object image is equal to the interval L1 in the reference image.

It is advantageous that the interval between the reference points is an average value of intervals of the reference points in the tomographic image or the interval between the reference points at both ends in the tomographic image. The interval of the reference points is of course not limited to the above and may be the interval between two reference points located at the center of the tomographic image.

When correcting the deviation of the magnification between the tomographic images, the calculation controller 70 corrects the magnification of the entire image as a first scheme. As a second scheme, the calculation controller 70 divides the tomographic image such that each feature area (reference point) makes a separation. The calculation controller 70 calculates the distance between the neighboring feature areas (the interval of the reference points) for each of the reference image and the object image. Then, the calculation controller 70 makes a comparison between these distances between the feature areas (the intervals of the reference points) that correspond to each other between the reference image and the object image. The calculation controller 70 corrects the deviation of the magnification for each divided area. It is noted that, when correcting the magnification, the calculation controller 70 corrects the interval of the A-scan forming the tomographic image. Thereby, it is possible to change the forming position of the A-scan signal in the tomographic image.

In such a way as described above, the displacement of the tomographic image is corrected for each A-scan. The corrected tomographic image is utilized for the creation of the averaging image. This allows the more accurate tomographic image (averaging image) to be obtained. For example, the calculation controller 70 sums the corrected tomographic images and derives the averaging thereof to obtain the averaging image.

Further, the calculation controller 70 is also able to use the displacement-corrected tomographic image to perform the analysis (for example, the layer thickness analysis). This allows a preferable analysis result to be obtained.

It is noted that any tomographic image may be defined as the tomographic image used for the reference image. For example, it is advantageous that the reference image is the tomographic image obtained under a state with little alignment deviation and fixation deviation. In this case, it is preferable that the OCT device 10 includes an anterior segment observing system. The OCT device 10 (the calculation controller 70) uses the anterior segment observing system to detect the alignment deviation. The preferable tomographic image is obtained by the use of the tomographic image with little alignment deviation as the reference image.

It is noted that the above-described scheme is advantageous in the case where the scanning position of the measurement light is corrected in response to the movement of the eye. For example, it is assumed that the first tomographic image is obtained in the scanning range of the measurement light around the optical axis of the OCT system. It is further assumed that the second tomographic image is obtained in the scanning range of the measurement light around the position shifted by ΔD (for example, 1 mm) from the optical axis of the OCT system. Even if the scanning position on the eye is corrected, there is a likelihood that the deviation of the magnification between the first tomographic image and the second tomographic image with respect to the scanning direction may occur due to the distortion of the OCT system. Therefore, as described above, the calculation controller 70 obtains the information of the deviation of the scanning width on the eye among the tomographic images. The calculation controller 70 corrects the magnification with respect to the scanning direction of the tomographic image based on the deviation information of the obtained scan width. Therefore, the deviation of the magnification is corrected.

<Displacement Detection Scheme>

The scheme for detecting the displacement between two images may be various image processing schemes. These schemes include the process using various correlation functions, the process utilizing the Fourier transform, and the process based on the matching of the feature points, for example.

For example, in one scheme, the predetermined reference image or the object image is shifted on a pixel basis and the reference image and the object image are compared. Then, the displacement direction and the displacement amount between both data when both data most match to each other (the correlation value is the highest) are detected. Further, in another scheme, from the predetermined reference image and the object image, the feature point common to these images is extracted. The displacement direction and the displacement amount of the extracted feature points are detected.

Further, the function for deriving the displacement between two images may be the phase-only correlation function. In this case, first, each image is Fourier-transformed, and the phase and the amplitude of each frequency component are obtained. It is noted that the obtained amplitude component is normalized so that the magnitude of the amplitude component to the frequency component is 1. Next, the phase difference is calculated between two images for each frequency. Then, the inverse Fourier transform is applied thereto.

Further, as illustrated in FIGS. 8A to 8C, when the incidence position on the eye is shifted in the direction orthogonal to the light axis L1, the difference in the optical path lengths of the measurement light between the center position and the peripheral position will be wider. This difference in the optical path lengths affects the forming position of the image with respect to the Z direction of the tomographic image, and appears as the distortion of the tomographic image. It is noted that, since the optical path length of the measurement light is different from the center to the peripheral as described above, there is a high likelihood that the A-scan signal positions do not match at the same position for each position in the scanning direction even if the correction of the position including the rotation of the image is applied on a pixel basis.

Further, the calculation controller 70 may correct the deviation of the magnification with respect to the scanning direction between the tomographic images by the comparison between the reference tomographic image and the object tomographic image.

Further, in the apparatus, the magnification-corrected tomographic image is used to obtain the averaging image. Thus, the distortion of the magnification between the tomographic images in the scanning direction can be appropriately corrected. As a result, the clear tomographic image with little noise can be obtained. Further, the tomographic image in which the magnification has been corrected by the above scheme is used to obtain the OCT three-dimensional data. Thus, the deviation of the magnification between the tomographic images in the scanning direction can be appropriately corrected. As a result, the preferable OCT three-dimensional data can be obtained. It is noted that the neighboring tomographic images are made of substantially the same organization and thus can be utilized for the correction.

Further, when correcting the magnification, the calculation controller 70 may correct the interval of the A-scans forming the tomographic image and change the forming position of the A-scan signal in the tomographic image.

Further, the method according to the present embodiment may be any of the following first to fifteenth methods:

The first method is a method for capturing a tomographic image of an eye using an optical coherence tomography, and has a step of obtaining a plurality of the tomographic images by the optical coherence tomography for obtaining an tomographic image of an examinee's eye by an optical scanning; a step of obtaining a displacement distribution between the plurality of obtained tomographic images for each A-scan; and a correction step for correcting the displacement between the tomographic images based on the obtained displacement distribution.

In the first method, the second method has a step of obtaining displacement information of an object tomographic image to a reference tomographic image in the plurality of tomographic images on an image basis; and a step of correcting the displacement between the tomographic images based on the obtained displacement information on an image basis.

In the third method in the first or second method, the step of obtaining the displacement distribution detects displacement information between the reference tomographic image and the object tomographic image in at least two or more areas and obtains the displacement distribution of the object tomographic image to the reference tomographic image for each A-scan. In the fourth method in any one of the first to third methods, the correction step changes the forming position of each A-scan in the tomographic image based on the obtained displacement distribution for each A-scan.

In any one of the first to fourth methods, the fifth method further has a step of obtaining an averaging image using a plurality of the tomographic images corrected by the correction step. In any one of the first to the fifth methods, the sixth method further has a step of obtaining a three-dimensional data using a plurality of the tomographic images corrected by the correction step.

In any one of the first to sixth methods, the seventh method further has a step for correcting a deviation of a magnification with respect to the scanning direction among the plurality of tomographic images obtained by the optical coherence tomography. In the eighth method in the seventh method, the step for correcting the deviation of the magnification corrects the deviation of the magnification based on the plurality of tomographic images.

In the seventh or eighth method, the ninth method further has a step of obtaining displacement information among tomographic images on an image basis; and a step of correcting the displacement among the tomographic images based on the obtained displacement information on an image basis. In the tenth method in any one of the seventh to ninth methods, the step for correcting the deviation of the magnification corrects the deviation of the magnification based on the distance between at least two or more feature points in the tomographic images.

In any one of the seventh to tenth methods, the eleventh method further has a step of obtaining an averaging image using a plurality of the tomographic image corrected by the step of correcting the deviation of the magnification. In any one of the seventh to the eleventh methods, the twelfth method further has a step of obtaining a three-dimensional data using a plurality of the tomographic images corrected by the step of correcting the deviation of the magnification. In the thirteenth method in any one of the seventh to the twelfth methods, the step of correcting the deviation of the magnification corrects the deviation of the magnification between the tomographic images with respect to the scanning direction based on the detection result from the eye movement detecting sensor for detecting the movement of the eye during an optical scanning.

The fourteenth method is a method for capturing a tomographic image of an eye using an optical coherence tomography, and has a step of obtaining a plurality of the tomographic images by an optical coherence tomography for obtaining the tomographic image of an examinee's eye by an optical scanning; and a step of correcting a deviation of the magnification among the plurality of the obtained tomographic images with respect to the scanning direction. In the fifteenth method in the fourteenth method, the method of correcting the deviation of the magnification corrects the deviation of the magnification based on the distance between at least two or more feature areas in each tomographic image.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

What is claimed is:

1. A method for capturing a tomographic image of an eye, the method comprising:

obtaining a plurality of tomographic images with respect to a same position of an examinee's eye, each of the plurality of tomographic images being obtained by an optical scanning in a lateral direction of the examinee's eye to obtain a plurality of A-scan signals in a depth direction of the examinee's eye and aligning the plurality of A-scan signals on a plane in the lateral direction to obtain each of the tomographic images;

selecting a reference tomographic image and an object tomographic image from the plurality of tomographic images;

dividing each of the reference tomographic image and the object tomographic image into a plurality of areas with respect to the lateral direction;

setting reference points of the reference tomographic image and reference points of the object tomographic image, each of the reference points being set on one of the plurality of A-scan signals in each of the plurality of areas;

obtaining displacements between the reference points of the reference tomographic image and the reference points of the object tomographic image;
obtaining an approximation straight line or an approximation curve of the reference points of the object tomographic image, the approximation straight line or the approximation curve indicating displacements in the lateral direction and the depth direction between the reference points of the reference tomographic image and the reference points of the object tomographic image;
moving each of the A-scan signals of the object tomographic image, on which the reference points are set, by the displacements in the lateral direction and the depth direction indicated by the approximation straight line or the approximation curve to correct the displacement among the tomographic images; and
moving each of the A-scan signals of the object tomographic image, on which the reference points are not set, by the displacements in the lateral direction and the depth direction indicated by the approximation straight line or the approximation curve to correct the displacement among the tomographic images.

2. The method according to claim 1, wherein the correcting the displacement among the tomographic images includes changing a forming position of an A-scan in the tomographic image based on the displacement distribution.

3. The method according to claim 1 further comprising:
obtaining an averaging image using a plurality of the displacement-corrected tomographic images.

4. The method according to claim 1 further comprising:
obtaining three-dimensional data using a plurality of the displacement-corrected tomographic images.

5. The method according to claim 1 further comprising:
correcting a deviation of a magnification with respect to a scanning direction among the plurality of tomographic images.

6. The method according to claim 5, wherein the correcting the deviation of the magnification includes correcting the deviation of the magnification based on the plurality of tomographic images.

7. The method according to claim 5, wherein the correcting the deviation of the magnification includes correcting the deviation of the magnification based on a distance between at least two or more feature areas in the tomographic images.

8. The method according to claim 5 further comprising:
obtaining an averaging image using a plurality of the magnification-corrected tomographic images.

9. The method according to claim 5 further comprising:
obtaining three-dimensional data using a plurality of the magnification-corrected tomographic images.

10. The method according to claim 5, wherein the correcting the deviation of the magnification includes:
detecting movement of the eye during an optical scanning; and
correcting the deviation of the magnification with respect to the scanning direction among the tomographic images based on the detection result.

11. A method for capturing tomographic image of an eye comprising:
obtaining a plurality of tomographic images with respect to a same position of an examinee's eye, each of the plurality of tomographic images being obtained by an optical scanning in a lateral direction of the examinee's eye to obtain a plurality of A-scan signals in a depth direction of the examinee's eye and aligning the plurality of A-scan signals on a plane in the lateral direction to obtain each of the tomographic images;
selecting a reference tomographic image and an object tomographic image from the plurality of tomographic images;
dividing each of the reference tomographic image and the object tomographic image into a plurality of areas with respect to the lateral direction;
setting reference points of the reference tomographic image and reference points of the object tomographic image, each of the reference points being set on one of the plurality of A-scan signals in each of the plurality of areas;
obtaining displacements between the reference points of the reference tomographic image and the reference points of the object tomographic image;
obtaining an approximation straight line or an approximation curve of the reference points of the object tomographic image, the approximation straight line or the approximation curve indicating displacements in the lateral direction and the depth direction between the reference points of the reference tomographic image and the reference points of the object tomographic image;
moving each of the A-scan signals of the object tomographic image, on which the reference points are set, by the displacements in the lateral direction and the depth direction indicated by the approximation straight line or the approximation curve to correct the displacement among the tomographic images;
moving each of the A-scan signals of the object tomographic image, on which the reference points are not set, by the displacements in the lateral direction and the depth direction indicated by the approximation straight line or the approximation curve to correct the displacement among the tomographic images; and
correcting a deviation of a magnification with respect to a scanning direction among the plurality of tomographic images based on the displacements between the reference points of the reference tomographic image and the reference points of the object tomographic image.

12. The method according to claim 11, wherein the correcting the deviation of the magnification includes calculating an interval between two of the reference points of the reference tomographic image and an interval between two of the reference points of the object tomographic image, and correcting the deviation of the magnification so that the interval between two of the reference points of the object tomographic image is equal to the interval between two of the reference points of the reference tomographic image.

* * * * *